(12) United States Patent
Bin (10) Patent No.: US 9,377,393 B2
(45) Date of Patent: Jun. 28, 2016

(54) METHOD FOR ELIMINATING HORIZONTAL OFFSET OF TRACTION TESTING DEVICE AND TRACTION TESTING DEVICE THEREOF

(75) Inventor: Weixiong Bin, Shenzhen (CN)

(73) Assignee: Weixiong Bin, Shenzhen (CN)

( * ) Notice: Subject to any disclaimer, the term of this patent is extended or adjusted under 35 U.S.C. 154(b) by 344 days.

(21) Appl. No.: 14/005,553

(22) PCT Filed: Mar. 18, 2012

(86) PCT No.: PCT/CN2012/072501
§ 371 (c)(1),
(2), (4) Date: Sep. 17, 2013

(87) PCT Pub. No.: WO2012/130057
PCT Pub. Date: Oct. 4, 2012

(65) Prior Publication Data
US 2014/0007648 A1    Jan. 9, 2014

(30) Foreign Application Priority Data

Mar. 25, 2011   (CN) .......................... 2011 1 0075750

(51) Int. Cl.
*G01N 19/02*    (2006.01)
*G01Q 60/36*    (2010.01)
*B82Y 35/00*    (2011.01)

(52) U.S. Cl.
CPC ................ *G01N 19/02* (2013.01); *B82Y 35/00* (2013.01); *G01Q 60/366* (2013.01); *G01N 2203/0286* (2013.01)

(58) Field of Classification Search
CPC ........... B82Y 35/00; G01N 2203/0286; G01Q 60/366; G01R 1/06705; G01R 1/0675
USPC ................................................. 73/842, 9, 827
See application file for complete search history.

(56) References Cited

U.S. PATENT DOCUMENTS

| 2,859,613 | A | * | 11/1958 | Green | G01L 1/2243 |
| | | | | | 177/211 |
| 3,199,345 | A | * | 8/1965 | Lee | G01L 1/22 |
| | | | | | 177/211 |
| 4,506,557 | A | * | 3/1985 | Jacobson | G01L 1/2206 |
| | | | | | 73/862.628 |
| 6,127,832 | A | * | 10/2000 | Comulada, Jr. | G01R 1/06705 |
| | | | | | 324/755.07 |
| 6,301,971 | B1 | * | 10/2001 | Sykes | G01N 3/00 |
| | | | | | 73/827 |
| 7,579,849 | B2 | * | 8/2009 | Kiesewetter | G01R 1/06705 |
| | | | | | 324/756.03 |
| 2014/0157909 | A1 | * | 6/2014 | Bin | G01N 3/24 |
| | | | | | 73/842 |

* cited by examiner

*Primary Examiner* — Hezron E Williams
*Assistant Examiner* — Nashmiya Fayyaz
(74) *Attorney, Agent, or Firm* — CBM Patent Consulting, LLC (57) ABSTRACT

A method for eliminating the horizontal offset of a traction force test device and traction force test device thereof, the device comprising a substrate (300), a first single-arm cantilever beam (100) and a second single-arm cantilever beam (100') which have the same structure. By employing an inverse horizontal displacement offset compensation structure, the invention completely overcomes the horizontal offset of the free end of the un-fixed single-arm cantilever beam, and achieves still better effect by suspending the test tool with two sets of inversely-installed cantilever beams which have the same structure and are arranged in the vertical direction.

7 Claims, 7 Drawing Sheets

METHOD FOR ELIMINATING HORIZONTAL OFFSET OF TRACTION TESTING DEVICE AND TRACTION TESTING DEVICE THEREOF

FIELD OF THE INVENTION

The invention relates to a traction force test device for testing the welding firmness of a semiconductor device with fine pitch and ultra fine pitch and the conducting wire or conductor thereof, and method for eliminating the horizontal offset of a test tool of the traction force test device.

BACKGROUND OF THE INVENTION

With the constant development of the semiconductor technology, more and more functions are integrated onto a small sized wafer substrate, and the wires laid on the wafer substrate are denser and denser. The device with 65 nm wide wires has been successfully developed at present, and the device with 45 nm wide wires will be produced in large scale finally. With the gradual popularization and application of the fine pitch or ultra fine pitch lead bonding technology, the space between a wire and a conductor becomes smaller and smaller, achieving 60-40 um, and even as small as 35-30 um within a few years in the future. As a result, a chip having the same size as before has more and more powerful functions nowadays.

The wire welded on a wafer usually has the diameter of 25.4 um/20 um or even thinner e.g. 18 um. And the diameter of a corresponding welding gold ball is 32 um-50 um. Those connecting wires and gold ball welding points must be firmly and reliably welded on a weld pad on a wafer substrate. The welded object to be tested is so small that a great part of the test force values are concentrated within the range from 2-3 g to 100 g. Therefore, how the test device ideally and conveniently applies a traction force test action to obtain a mechanical test result appropriating to the firmness of the tested object to the most extent, has become an issue worth to study in this field.

A known test device uses a thin hooked needle to hook the welding lead to be tested in the IC via a force sensor, and does pull and push actions to measure the firmness of the welding lead or the strength of the lead itself in a destructive or non-destructive manner. The basic principle is very simple. However in fact, the requirements for the test in the practical process are far from as simple as mentioned in the above principle.

Figure 1:
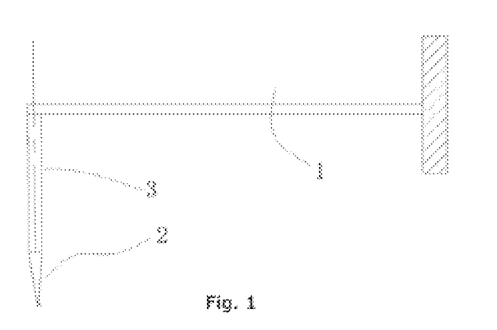
FIG. 1 is the schematic diagram of the structure of an existing force sensor.
Figure 2:
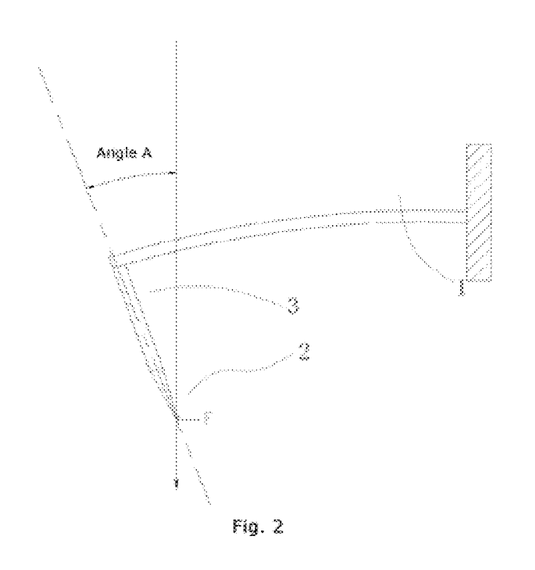
FIG. 2 is the schematic diagram of the structure of the deformed force sensor as shown in FIG. 1.

The force sensor can deform whenever under stress, thus the magnitude of the test force can be identified according to the deformation of an elastic body. A former test instrument uses a force sensor having a cantilever beam structure as shown in FIG. 1; a test tool 3 with a certain length and having a very thin hook 2 arranged at the tip is installed at the front end of the cantilever beam 1; when a test force is applied onto the test tool 3, the force sensor of the cantilever beam structure bends and deforms under the effect of the test force F. Different levels of test forces cause different degrees of bending deformation. The rigid test tool 3 installed at the front end of the sensor forms a rotation angle A (as shown in FIG. 2) in the direction of the test force F, which is unexpected for the test itself, thus influencing the truthfulness of the test result. The quantitative association between the degrees of bending deformation, the rotation angle A and the test force will not be discussed herein. As a matter of fact, it is extraordinarily complex to accurately quantify the above association. However, it is obvious that the test tool may cause awful things due to the rotation angle A generated along with the bending deformation of the force sensor of the cantilever beam: during the test of a product with dense welding leads in the IC, the hook 2 at the front end of the test tool 3 having the rotation angle A may cause damage to the welding lead in an un-tested IC beside.

Figure 3:
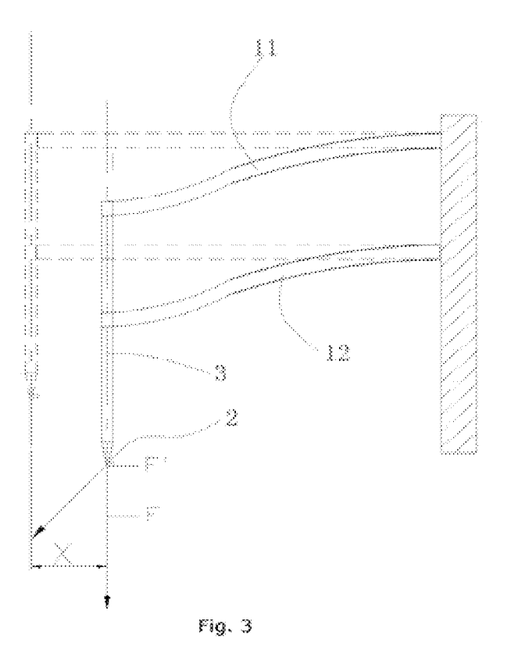
FIG. 3 is the schematic diagram of the structure of a second existing force sensor.

Another solution for testing the traction of the welding lead in the IC by employing a force sensor with double cantilever beams having the same length is as shown in FIG. 3. Under the effect of the test force F, the first cantilever beam 11 and the second cantilever beam 12 with the same length have almost the same bending deformation, so the test tool 3 and the hook 2 at the front end thereof can still maintain the vertical attitude, thus avoiding the occurrence of the rotation angle A as mentioned above. However, it can also be easily observed that the test tool 3 and the hook 2 at the front end thereof have a displacement X. That is to say, during the test of a product with dense welding leads in the IC, the hook 2 at the front end of the test tool may still cause damage to the welding lead in an un-tested IC beside. The dashed line part in the figure is the state of the force sensor when the test force F is not applied.

Figure 4:
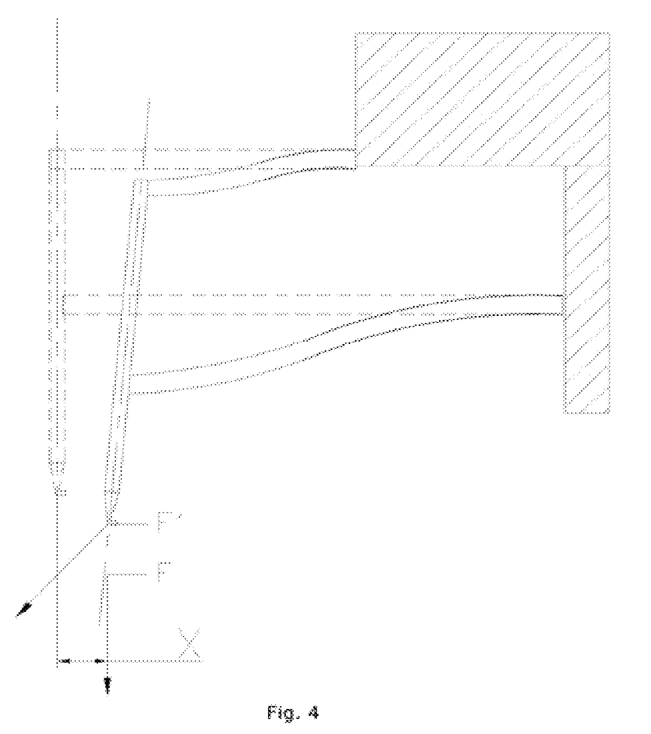
FIG. 4 is the schematic diagram of the structure of a third existing force sensor.

An U.S. patent: U.S. Pat. No. 6,301,971 provides another solution: employing a force sensor with double cantilever beams having unequal lengths. As shown in FIG. 4, under the effect of the test force F, the unequal first cantilever beam 11 and second cantilever beam 12 have different bending deformations due to the different lengths. The specific and accurate relationship between the bending deformation and the applied test force is extraordinarily complex. As for the force sensor with double cantilever beams having unequal lengths, when the test force is applied, the test tool 3 and the hook 2 at the front end thereof will rotate in a pre-designed inclination direction, with the purpose of coinciding the axial direction of the test tool 3 and the hook 2 with the direction of the test force F. However, the prerequisite of the force sensor with double cantilever beams is supposing that the direction of the test force F is inclined. In practice, the directions of the test forces are various, for example, the direction of the hypothetical test force F and the gravity direction of a weight hung for calibrating the sensor; the direction of the test force is difficult to be ensured to coincide with the axial line of the test tool. However, due to the specially designed deflection angle of the test tool when under stress, the offset X at the front end of the test tool has a decreasing trend, thus better reducing the possibility of causing damage to the welding lead in the un-tested IC beside compared with the above solutions. However, the analysis from the principle shows that offset X will still occur at the front end of the test tool 3.

BRIEF DESCRIPTION OF THE INVENTION

Aiming to overcome the above defects, the invention provides the society with a method having horizontal displacement compensation and neutralization functions during traction force test, and capable of eliminating the traction force test device horizontal offset in principle.

The invention secondly aims to provide a traction force test mechanism capable of ensuring the traction force test to be more reliable and accurate.

The basic thought of the invention is to introduce into the sensor employed by the invention a mechanism capable of actively and naturally compensating the inverse horizontal displacement offset, so as to reduce the offset occurred during the test to the most extent in principle. The inversely installed first single-arm cantilever beam and second single-arm cantilever beam in the invention respectively bend and have the horizontal displacement X1 and X2 occurred in the front under the effect of the same level test force F. Obviously, the displacement directions of the horizontal displacements X1 and X2 are opposite. Under the circumstance that the first single-arm cantilever beam and the second single-arm cantilever beam have the same structure, the horizontal displacements X1 and X2 not only have the opposite displacement directions, but also have the same displacement. If the inversely installed first single-arm cantilever beam and the second single-arm cantilever beam are integrated, that is: the first single-arm cantilever beam and the second single-arm cantilever beam are arranged in parallel; the two ends on the same side of the first single-arm cantilever beam and the second single-arm cantilever beam are fixedly connected; and then the other end of the first single-arm cantilever beam or the second single-arm cantilever beam is fixed on a substrate; the fixed end is defined as the fixed end of the fixed single-arm cantilever beam, and the remaining end is defined as the free end of the un-fixed single-arm cantilever beam; the free end of the un-fixed single-arm cantilever beam is connected with a test tool; when a test force F is applied onto the free end of the un-fixed single-arm cantilever beam, the horizontal offset X1 away from the perpendicular line of the test tool generated by the free end of the un-fixed single-arm cantilever beam, will be neutralized by the horizontal offset X2 heading to the perpendicular line of the test tool generated by the free end of the fixed single-arm cantilever beam, so that the free end of the un-fixed single-arm cantilever beam only has vertical displacement but has no horizontal offset, thus completely overcoming horizontal offset of the free end of the un-fixed single-arm cantilever beam.

In order to ensure the test tool to be upright during move as a whole without generating swaying phenomenon, two groups of inversely installed same cantilever beams are used: the first cantilever beam and the second cantilever beam are a group, and the third cantilever beam and the fourth cantilever beam are the other group; the first cantilever beam is fixed on the substrate; the free end of the first cantilever beam and the fixed end of the second cantilever beam are fixed together; the third cantilever beam and the first cantilever beam are fixed on the substrate at intervals in the vertical direction; the free end of the third cantilever beam and the fixed end of the fourth cantilever beam are fixed together; the test tools are respectively fixed at the free ends of the first cantilever beam and the fourth cantilever beam. When the test force F is applied onto the test tool, the horizontal displacement summation of the first cantilever beam, the second cantilever beam, the third cantilever beam, and the fourth cantilever beam is neutralized at the free end of the second cantilever beam and the free end of the fourth cantilever beam, i.e. the horizontal offsets of the test tool is neutralized. The test tool only has vertical displacement H, but has no horizontal offset or the appearance of test tool rotation angle. The horizontal displacement X of the free end E1 of the first cantilever beam and the free end E2 of the third cantilever beam has no influence on the test, therefore it will not be considered any more, thus, avoiding the possibility of damaging the un-tested welding lead beside the welding lead in the IC to the most extent during traction force test. In addition, the test tool maintains the vertical attitude and has no horizontal displacement all the time during the test, therefore the mechanical test performance of the test system and the reliability of the test result are significantly optimized. In the above description, one end of the first cantilever beam and one end of the third cantilever beam are fixed on the substrate, and the free ends of the second cantilever beam and the fourth cantilever beam are connected with the test tool. In practical application, the following design is also feasible: one end of the second cantilever beam and one end of the fourth cantilever beam are fixed on the substrate, and the free ends of the first cantilever beam and the third cantilever beam are connected with the test tool. This kind of structure has the same effect, so no detailed analysis will be given herein any more.

The specific technical solution of the invention is: providing a method for eliminating the horizontal offset of a traction force test device, and forming a whole force sensor by inversely installing the fixed end of the second cantilever beam at the free end of the first cantilever beam, and vertically installing the test tool and the hook at the free end of the second cantilever beam. The free end of the second cantilever beam is the free end (test force applied end) of the force sensor; the fixed end of the first cantilever beam is the fixed end of the force sensor, and is fixed on a movable substrate. When a test force is applied onto the free end (test tool and hook) of the force sensor, the horizontal displacement of the free end (test tool and hook) of the force sensor is compensated or neutralized via the inverse horizontal displacement X1 and X2 of the first cantilever beam and the second cantilever beam, so as to achieve the objective that the free end (test tool and hook) of the force sensor only has vertical displacement but has no horizontal displacement when the test force is applied, thus ensuring the safety of the test and the reliability of the test data.

In order to guarantee the test effect, the utility mechanism of the invention employs two sets of inversely installed cantilever beams: the first cantilever beam and the second cantilever beam; as well as the third cantilever beam and the fourth cantilever beam. The fixed end of the second cantilever beam is inversely fixed at the free end of the first cantilever beam; and the fixed end of the fourth cantilever beam is inversely fixed at the free end of the third cantilever beam. The fixed end of the first cantilever beam and the fixed end of the third cantilever beam are fixed on the movable substrate; and the free end of the second cantilever beam is connected with the free end of the fourth cantilever beam. The test tool and the hook are vertically installed at the free end of the second cantilever beam and the free end of the fourth cantilever beam, and extend out downward. In order to conveniently rotate the test tool and the hook, a micro rotary motor is also installed on the test tool to drive the test tool and the hook to rotate, which will not be over-detailed in the specification due to the universal design thereof. Under the circumstance that the measurement range of the test force is small, an anti-vibration damper, such as magnetic field damper, liquid or gas damper and the like, can be applied onto the free end the force sensor consisting of the first cantilever beam and the second cantilever beam, and can also be applied onto the free ends of the force sensors consisting of the first cantilever beam, the second cantilever beam and the third cantilever beam, the fourth cantilever beam, so as to reduce the interference caused by the vibration of the environment or the vibration of the test system itself.

In order to achieve the second objective of the invention, also provided is a traction force test device, comprising a substrate, a first single-arm cantilever beam and a second single-arm cantilever beam which have the same structure; the first single-arm cantilever beam and the second single-arm cantilever beam are arranged in parallel; the two ends on the same side of the first single-arm cantilever beam and the second single-arm cantilever beam are fixedly connected; the other end of the first single-arm cantilever beam or the second single-arm cantilever beam is fixed on the substrate; and the remaining free end of the un-fixed single-arm cantilever beam is connected with the test tool with a hook.

A third single-arm cantilever beam and a fourth single-arm cantilever beam which have the same structure are arranged at intervals in the vertical direction of the first single-arm cantilever beam and the second single-arm cantilever beam; the third single-arm cantilever beam and the fourth single-arm cantilever beam are arranged in parallel; the two ends on the same side of the third single-arm cantilever beam and the fourth single-arm cantilever beam are fixedly connected; the other end of the third single-arm cantilever beam or the fourth single-arm cantilever beam is fixed on the substrate; and the remaining free end of the un-fixed single-arm cantilever beam is connected with the test tool with a hook.

An anti-vibration damper for reducing the vibration of the environment or the vibration of the test system itself is applied onto the free end of the un-fixed single-arm cantilever beam.

The test tool is also provided with a micro rotary motor thereon for rotating the test tool and the hook.

The first single-arm cantilever beam and the second single arm cantilever beam are both made of aluminum material.

The first single-arm cantilever beam, the second single-arm cantilever beam, the third single-arm cantilever beam and the fourth single-arm cantilever beam are all made of aluminum material.

The anti-vibration damper is a magnetic field damper, a liquid or a gas damper.

The two ends on the same side of the first single-arm cantilever beam and the second single-arm cantilever beam are fixedly connected, forming a U-shape; the two ends on the same side of the third single-arm cantilever beam and the fourth single-arm cantilever beam are fixedly connected, also forming a U-shape.

The invention employs a method for actively and naturally compensating the inverse horizontal displacement offset, so as to reduce the offset occurred during the test to the most extent in principle, and employs at least one set of inversely installed cantilever beam in the following structure: the first single-arm cantilever beam and the second single-arm cantilever beam are arranged in parallel; the two ends on the same side of the first single-arm cantilever beam and the second single-arm cantilever beam are fixedly connected; the other end of the first single-arm cantilever beam or the second single-arm cantilever beam is fixed on the substrate; and the remaining free end of the un-fixed single-arm cantilever beam is connected with the test tool with a hook. Therefore, when the test force F is applied onto the free end of un-fixed single-arm cantilever beam, the horizontal offset X1 away from the perpendicular line of the test tool generated by the free end of the un-fixed single-arm cantilever beam, will be neutralized by the horizontal offset X2 heading to the perpendicular line of the test tool generated by the free end of the fixed single-arm cantilever beam, so that the free end of the un-fixed single-arm cantilever beam only has vertical displacement but has no horizontal offset, thus completely overcoming horizontal offset of the free end of the un-fixed single-arm cantilever beam, and achieving still better effect by suspending the test tool with two sets of inversely-installed cantilever beams which have the same structure and are arranged in the vertical direction.

DETAILED DESCRIPTION OF THE INVENTION

Figure 5:
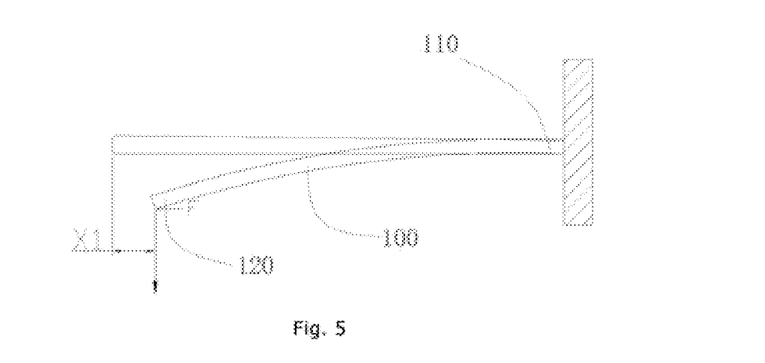
FIG. 5 and FIG. 6 are the schematic diagram of the structure of the invention.
Figure 6:
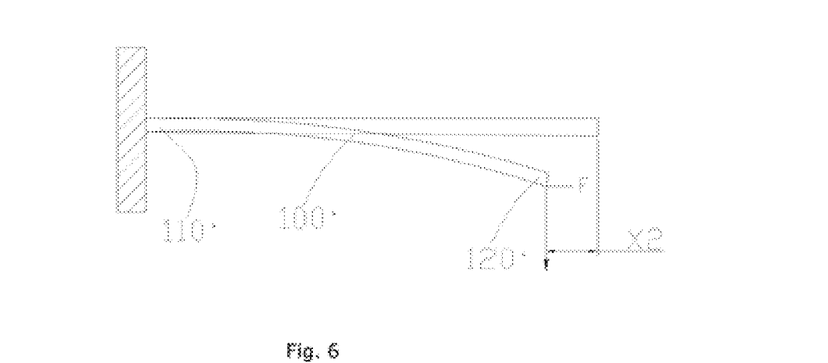

A method for eliminating the horizontal offset of a traction force test device, the method introducing a mechanism capable of actively and naturally compensating the inverse horizontal displacement offset, so as to reduce the offset occurred during the test to the most extent in principle. As shown in FIG. 5 and FIG. 6, the first single-arm cantilever beam 100 and the second single-arm cantilever beam 100' are inversely installed; the fixed ends 110, 110' of the first single-arm cantilever beam 100 and the second single-arm cantilever beam 100' are fixed; and free ends 120, 120' of the first single-arm cantilever beam 100 and the second single-arm cantilever beam 100' respectively bend and have the horizontal displacement X1 and X2 occurred in the front under the effect of the same level test force F. Obviously, the horizontal displacement X1 and X2 have the same magnitude, but have different directions. Under the circumstance that the first single-arm cantilever beam 100 and the second single-arm cantilever beam 100' have the same structure, the displacement. X1 and X2 not only have the opposite directions, but also have the same displacement.

Figure 7:
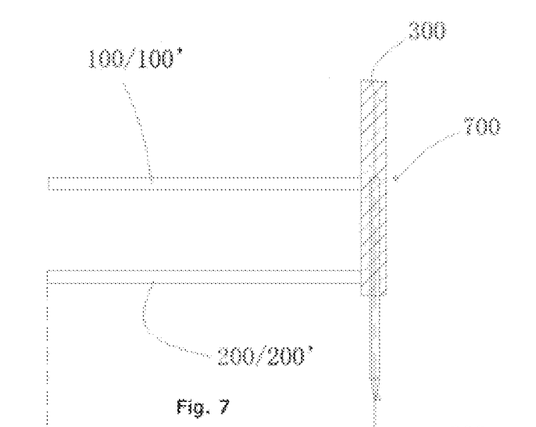
FIG. 7 and FIG. 8 are the schematic diagram of the structure of the invention after the FIG. 5 and the FIG. 6 are integrated.
Figure 8:
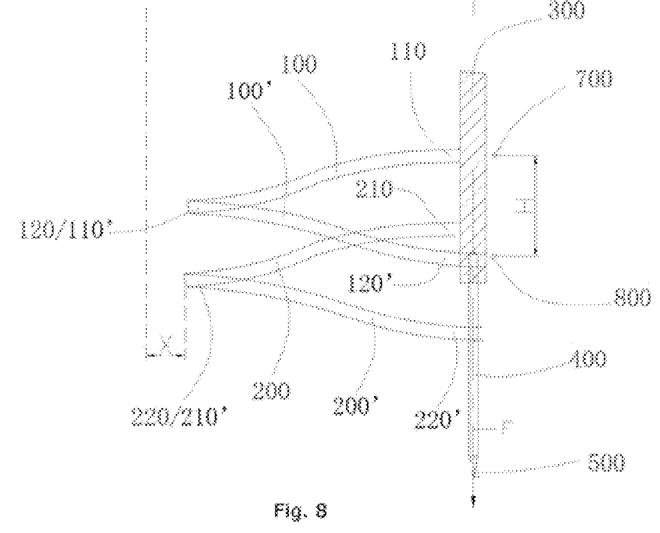

If the inversely installed first single-arm cantilever beam 100 and the second single-arm cantilever beam 100' are integrated (as shown in FIG. 7 and FIG. 8), that is: the first single-arm cantilever beam 100 and the second single-arm cantilever beam 100' which have the same structure are arranged in parallel with the two ends aligned; the two ends on the same side of the first single-arm cantilever beam 100 and the second single-arm cantilever beam 100', i.e. the free end 120 of the first single-arm cantilever beam 100 and the fixed end 110' of the second single-arm cantilever beam 100' are fixedly connected; and then the other end of the first single-arm cantilever beam 100 or the second single-arm cantilever beam 100', i.e. the fixed end 110 of the first single-arm cantilever beam 100 as shown in the figure is fixed; the fixed end is defined as the fixed end of the fixed single-arm cantilever beam, and the remaining end is defined as the free end of the un-fixed single-arm cantilever beam, i.e. the free end 120' of the second single-arm cantilever beam 100' as shown in the figure. When the test force F is applied onto the free end of the un-fixed single-arm cantilever beam, the horizontal offset X1 away from the perpendicular line of the test tool generated by the free end of the un-fixed single-arm cantilever beam, will be neutralized by the horizontal offset X2 heading to the perpendicular line of the test tool generated by the free end of the fixed single-arm cantilever beam. Because the first single-arm cantilever beam 100 and the second single-arm cantilever beam 100' have consistent performances, the free end of the un-fixed single-arm cantilever beam only has vertical displacement, but has no horizontal offset.

In order to ensure the test tool to be upright during move as a whole, two groups of inversely installed same cantilever beams are used: the first cantilever beam 100 and the second cantilever beam 100' are a group, and the third cantilever beam 200 and the fourth cantilever beam 200' are the other group; as shown in FIG. 7 and FIG. 8, the fixed end 110 of the first cantilever beam 100 is fixed on the substrate 300; the free end 120 of the first cantilever beam 100 and the fixed end 110' of the second cantilever beam 100' are fixed together; the third cantilever beam 200 and the first cantilever beam 100 are arranged at intervals in the vertical direction of the first cantilever beam 100 and the second cantilever beam 100; the fixed end 210 of the third cantilever beam 200 is fixed on the substrate 300; the free end 220 of the third cantilever beam 200 and the fixed end 210' of the fourth cantilever beam 200' are fixed together; the test tools 400 are respectively fixed at the free ends 120', 220' of the second cantilever beam 100' and the fourth cantilever beam 200'. When the test force F is applied onto the test tool 400, the horizontal displacement summation of the first cantilever beam 100, the second cantilever beam 100', the third cantilever beam 200, and the fourth cantilever beam 200' is neutralized at the free end 120' of the second cantilever beam 100' and the free end 220' of the fourth cantilever beam 200', i.e. the horizontal offsets of the test tool 400 is neutralized. The test tool 400 only has vertical displacement H (i.e. from the position 700 of the test tool before being stressed to the position 800 of the test tool after being stressed), but has no horizontal offset or the appearance of test tool 400 rotation angle. The horizontal displacement X of the free end 110' of the first cantilever beam 100 and the free end 210' of the third cantilever beam 200 has no influence on the test, therefore it will not be considered any more, thus, avoiding the possibility of damaging the un-tested welding lead beside the welding lead in the IC to the most extent during traction force test. In addition, the test tool maintains the vertical attitude and has no horizontal displacement all the time during the test, therefore the mechanical test performance of the test system and the reliability of the test result are significantly optimized.

Figure 9:
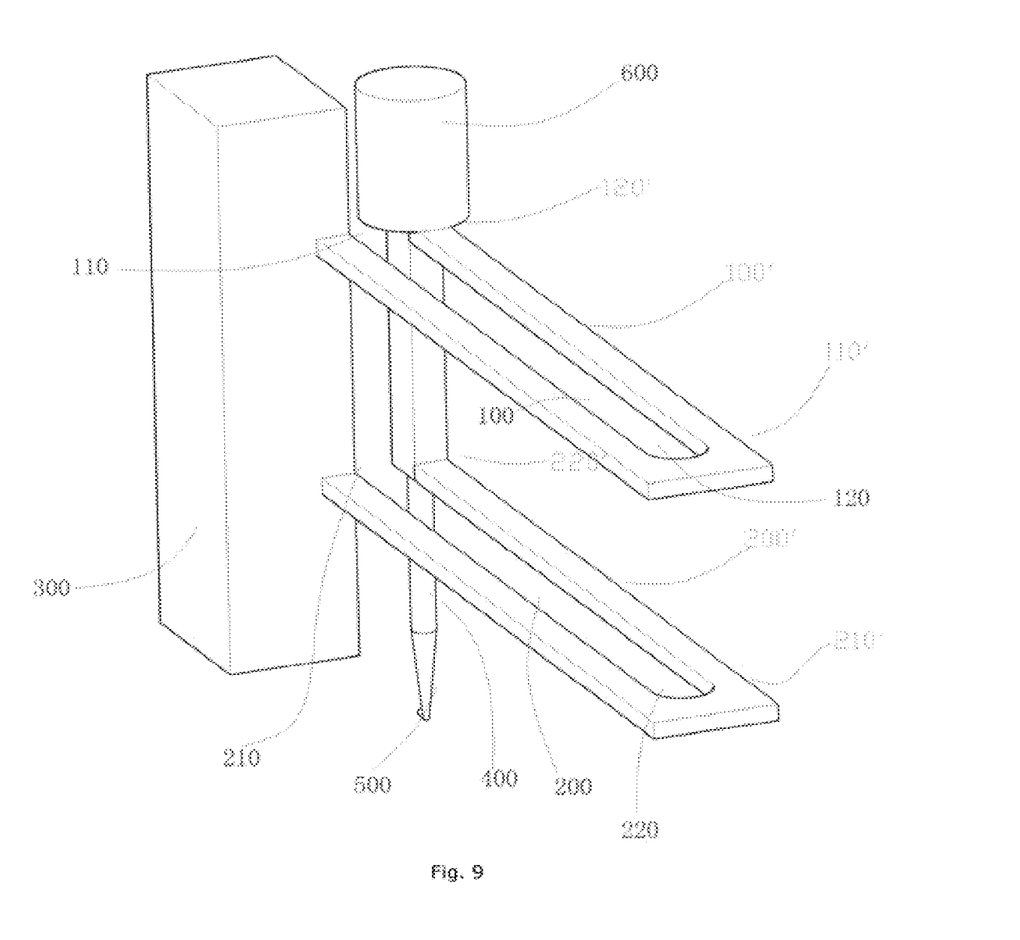
FIG. 9 is the schematic diagram of the stereoscopic structure of an embodiment of the invention.
Figure 10:
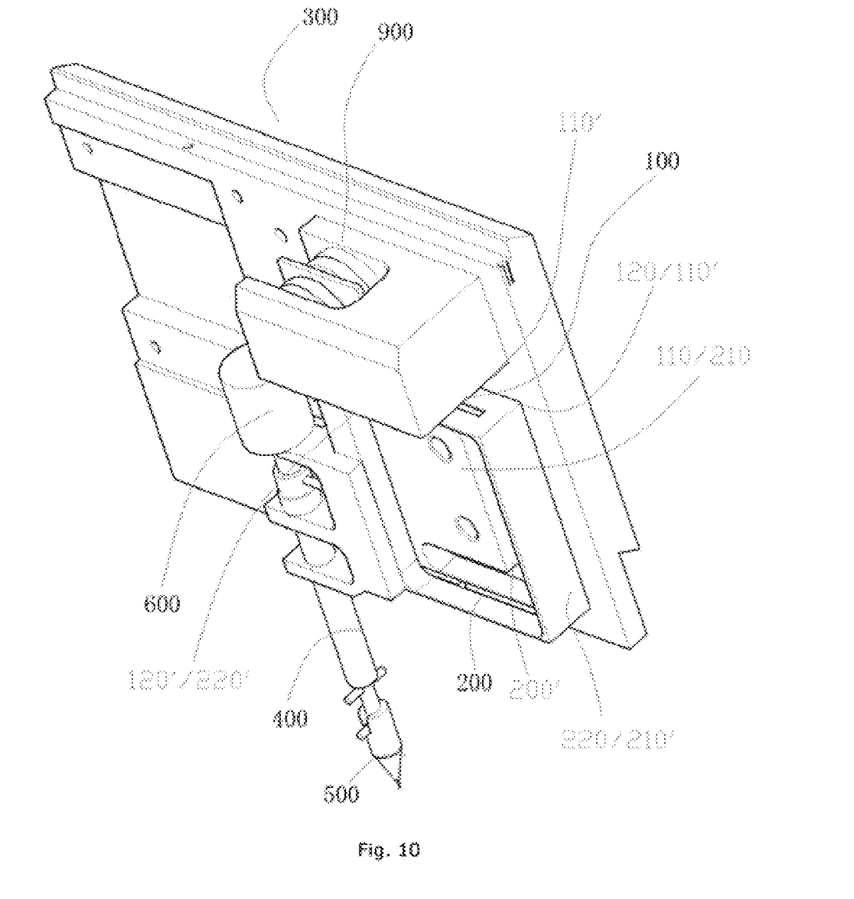
FIG. 10 is the schematic diagram of the stereoscopic structure of a preferable embodiment of the invention.

Please refer to FIG. 9 and FIG. 10 which represent a traction force test device. The device comprises and a substrate 300, a first single-arm cantilever beam 100 and a second single-arm cantilever beam 100' which have the same structure; the first single-arm cantilever beam 100 and the second single-arm cantilever beam 100' are arranged in parallel; the two ends on the same side of the first single-arm cantilever beam 100 and the second single-arm cantilever beam 100' are fixedly connected, that is, the free end 120 of the first single-arm cantilever beam 100 is fixedly connected with the fixed 110' of the second single-arm cantilever beam 100', forming a U-shaped structure; the other end (the fixed end 110 of the first single-arm cantilever beam 100 in the embodiment) of the first single-arm cantilever beam 100 (or the other end of the second single-arm cantilever beam 100') is fixed on the substrate 300; and the remaining free end (the free end 120' of the second single-arm cantilever beam 100' in the embodiment) of the un-fixed single-arm cantilever beam is connected with the test tool 400 with a hook 500. In order to guarantee the test effect and prevent the test tool 400 with a hook 500 from swaying, a third single-arm cantilever beam 200 and a fourth single-arm cantilever beam 200' which have the same structure are arranged at intervals in the vertical direction of the first single-arm cantilever beam 100 and the second single-arm cantilever beam 100; the third single-arm cantilever beam 200 and the fourth single-arm cantilever beam 200' are arranged in parallel; the two ends on the same side of the third single-arm cantilever beam 200 and the fourth single-arm cantilever beam 200' are fixedly connected, that is, the free end 220 of the third single-arm cantilever beam 200 is fixedly connected with the fixed 210' of the fourth single-arm cantilever beam 200', forming a U-shaped structure; the other end (the fixed end 210 of the third single-arm cantilever beam 200 in the embodiment) of the third single-arm cantilever beam 200 (or the fourth single-arm cantilever beam 200') is fixed on the substrate 300; and the remaining free end (the free end 220' of the fourth single-arm cantilever beam 200' in the embodiment) of the un-fixed single-arm cantilever beam is connected with the test tool 400 with a hook 500. An anti-vibration damper 900 for reducing the vibration of the environment or the vibration of the test system itself is applied onto the free end of the un-fixed single-arm cantilever beam (i.e. the free end 120' of the second single-arm cantilever beam 100' and the free end 220' of the fourth single-arm cantilever beam 200'). The anti-vibration damper 900 in the embodiment is a magnetic field damper. Obviously, the magnetic field damper can also be replaced by a liquid or a gas damper as required.

In the present embodiment, the test tool 400 is also provided with a micro rotary motor 600 thereon for rotating the test tool 400 and the hook 500. In the present invention, the first single-arm cantilever beam 100, the second single-arm cantilever beam 100', the third single-arm cantilever beam 200 and the fourth single-arm cantilever beam 200' can all be made of aluminum material or aluminum alloy material.

What is claimed is:

1. A method for eliminating the horizontal offset of a traction force test device, comprises at least four single-arm cantilever beams which are grouped as two sets; wherein a first set of single-arm cantilever beams (100/100') whose ends are fixedly connected in parallel; wherein one free end of the first set of single-arm cantilever beams (100/100') is connected with a test tool while other free end is fixed on a substrate; wherein when a test force F being applied onto the end of the first set of single-arm cantilever beams connected with the test tool, horizontal offset X1 away from the perpendicular line to the test tool, is neutralized by horizontal offset X2 heading to the perpendicular line to the test tool generated by the end of the first set of single-arm cantilever beams connected on the substrate, so that the end of the first set of single-arm cantilever beams connected with the test tool only having a vertical displacement to the test tool but not having a horizontal offset; a second set of single-arm cantilever beams (200/200') arranged at intervals in a same direction to the first set of single-arm cantilever beams (100)100'); wherein the two single-arm cantilever beams (200/200') of the second set of single-arm cantilever beams (200/200') is fixedly connected with ends in parallel; and one free end of the second set of single-arm cantilever beams (200/200') is connected with the test tool with a hook while other free end of the second set of single-arm cantilever beams (200/200') is fixed on the substrate; wherein when the test force F being applied onto the end of second set of single-arm cantilever beams (200/200') connected with the test tool, the horizontal offset X1 away from the perpendicular line to the test tool generated by the end of second set of single-arm cantilever beams (200/200') connected with the test tool, is neutralized by the horizontal offset X2 heading to the perpendicular line to the test tool generated by the end of the second set of single-arm cantilever beams (200/200') connected on the substrate, so that the end of the second set of single-arm cantilever beams (200/200') connected with the test tool only having the vertical displacement to the test tool but not having the horizontal offset.

2. A traction force test device, comprises a substrate (300) and four single-arm cantilever beams which are grouped as two sets, wherein a first set of single-arm cantilever beams (100/100') are arranged in parallel and) fixedly connected by ends of two single-arm cantilever beams of the first set of single-arm cantilever beams (100/100'); and one free end of the first set of single-arm cantilever beams (100/100') is connected with a test tool while other free end of the first set of single-arm cantilever beams (100/100') is fixed on a substrate; wherein when a test force F being applied onto the end of the first set of single-arm cantilever beams connected with the test tool, horizontal offset X1 away from the perpendicular line to the test tool, is neutralized by horizontal offset X2 heading to the perpendicular line to the test tool generated by the end of the first set of single-arm cantilever beams connected on the substrate, so that the end of the first set of single-arm cantilever beams connected with the test tool only having a vertical displacement to the test tool but not having a horizontal offset; a second set of single-arm cantilever beams (200/200') arranged at intervals in a same direction of the first set of single-arm cantilever beams (100/100') in parallel; wherein two single-arm cantilever beams (100/100') of the second set of single-arm cantilever beams (200/200') is fixedly connected by ends of the two single-arm cantilever beams of the second set of single-arm cantilever beams (200/200'); and one free end of the second set of single-arm cantilever beams is connected with the test tool with a hook while other free end of the second set of single-arm cantilever beams is fixed on the substrate; wherein when the test force F being applied onto the end of second set of single-arm cantilever beams (200/200') connected with the test tool, the horizontal offset X1 away from the perpendicular line to the test tool generated by the end of second set of single-arm cantilever beams (200/200') connected with the test tool, is neutralized by the horizontal offset X2 heading to the perpendicular line to the test tool generated by the end of the second set of single-arm cantilever beams (200/200') connected on the substrate, so that the end of the second set of single-arm cantilever beams (200/200') connected with the test tool only having the vertical displacement to the test tool but not having the horizontal offset.

3. The traction force test device as claimed in claim 2, is characterized in that: an anti-vibration damper for reducing vibration of environment or vibration of a test system itself is applied onto end of the single-arm cantilever beam connected with the test tool of single-arm cantilever beam.

4. The traction force test device as claimed in claim 3, is characterized in that: the test tool (400) is also provided with a micro rotary motor (600) thereon for rotating the test tool (400) and the hook (500).

5. The traction force test device as claimed in claim 2, is characterized in that: the single-arm cantilever beams are all made of aluminum material.

6. The traction force test device as claimed in claim 3, is characterized in that: the anti-vibration damper for reducing vibration of environment or vibration of the test system itself is a magnetic field damper, a liquid or a gas damper.

7. The traction force test device as claimed in claim 2, is characterized in that: the two ends of two single-arm cantilever beams (100/100') of the first set of single-arm cantilever beams is fixedly connected to form a U-shape; the two ends of two single-arm cantilever beams (200/200') of the second set of single-arm cantilever beams (200/200') is fixedly connected to form a U-shape.

* * * * *